US00PP08464P

United States Patent [19]

VandenBerg

[11] Patent Number: Plant 8,464

[45] Date of Patent: Nov. 16, 1993

[54] CHRYSANTHEMUM PLANT NAMED PELEE

[75] Inventor: Cornelis P. VandenBerg, Salinas, Calif.

[73] Assignee: Yoder Brothers, Inc., Barberton, Ohio

[21] Appl. No.: 935,267

[22] Filed: Aug. 27, 1992

[51] Int. Cl.[5] ..... A01H 5/00

[52] U.S. Cl. ..... Plt./74.1

[58] Field of Search ..... Plt./74.1, 82.2, 82.3

*Primary Examiner*—Howard J. Locker

*Attorney, Agent, or Firm*—Foley & Lardner

[57] ABSTRACT

A Chrysanthemum plant named Pelee particularly characterized by its flat capitulum form; daisy capitulum type bi-colored red and yellow ray floret color; diameter across face of capitulum of 114 to 124 mm when fully opened, when grown as a pinched disbudded pot mum; photoperiodic flowering response to short days of 54 to 62 days; plant height with 15 to 16 long days after sticking unrotted cuttings, and with 0 to 2 applications of 2500 ppm B-9 SP, ranges from 23 to 28 cm when grown as a pinched pot mum with 4 cuttings in a 15 cm pot; branching pattern is semi-spreading, each plant having 3 to 4 laterals after pinch; and recommended as disbud pot mum.

3 Drawing Sheets

The present invention comprises a new and distinct cultivar of Chrysanthemum, botanically known as *Dendranthema grandiflora,* referred to by the cultivar name Pelee.

Pelee, identified as 5143 (88-122001), was originated from a cross made by Cornelis P. VandenBerg in a controlled breeding program in Salinas, Calif., in 1986.

The female parent of Pelee was an unnamed seedling identified as 5211 (82-404009), and described as a yellow disbud daisy pot mum with a flowering response of 53 to 59 days under normal conditions in Salinas, Calif.; plant height of 23 to 28 cm with 15 to 16 long days after sticking unrooted cuttings prior to start of short days and with one to two applications of 2500 ppm B-9 SP when grown as a pinched pot mum; branching habit of 3 to 5 laterals developing after pinch; and diameter of capitulum of 133 to 149 mm. The female parent was discarded from all programs on May 28, 1992.

The male parent of Pelee was an unnamed seedling, identified as 5548 (82-H59007), and described as a red flat disbud daisy pot mum with a flowering response to short days of 52 to 56 days under normal conditions in Salinas, Calif.; plant height of 25 to 30 cm with 15 to 16 long days after sticking unrooted cuttings prior to start of short days and 1 to 3 applications of 2500 ppm B-9 SP when grown as a pinched pot mum; branching habit of 4 to 5 laterals developing after pinch; and diameter of capitulum of 114 to 117 mm.

Pelee was discovered and selected as one flowering plant within the progeny of the stated cross by Cornelis P. VandenBerg in October 1988, in a controlled environment in Salinas, Calif.

The first act of asexual reproduction of Pelee was accomplished when vegetative cuttings were taken from the initial selection in December 1988 in a controlled environment in Salinas, Calif., by technicians working under supervision of Cornelis P. VandenBerg.

Horticultural examination of controlled flowerings of successive plantings has shown that the unique combination of characteristics as herein disclosed for Pelee are firmly fixed and are retained through successive generations of asexual reproduction.

Pelee has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of Pelee, which, in combination, distinguish this Chrysanthemum as a new and distinct cultivar:

1. Flat capitulum form.
2. Daisy capitulum type.
3. Bi-colored red and yellow ray floret color.
4. Diameter across face of capitulum of 114 to 124 mm when fully opened, when grown as a pinched disbudded pot mum.
5. Photoperiodic flowering response to short days of 54 to 62 days.
6. Plant height with 15 to 16 long days after sticking unrooted cuttings, and with 0 to 2 applications of 2500 ppm B-9 SP, ranging from 23 to 28 cm when grown as a pinched pot mum with 4 cuttings in a 15 cm pot.
7. Branching pattern is semi-spreading, each plant having 3 to 4 laterals after pinch.
8. Recommended as disbud pot mum.

The accompanying photographic drawings show typical inflorescence and leaf characteristics of Pelee, with the colors being as nearly true as possible with illustrations of this type.

Sheet 1 is a top perspective color photograph of Pelee grown as a pinched spray pot mum with 4 cuttings in a 15 cm pot.

Sheet 2 is a black and white photograph of three views of the infloresncence of Pelee.

Sheet 3 is a black and white photograph showing the upper and under sides of the leaves of Pelee at 3 stages of development (mature, intermediate and immature). In sheets 2 and 3 a measuring tape in centimeters has been added.

No commercial varieties known to the inventor can be compared with Pelee. The combination of capitulum form and type and the red and yellow bi-colored ray floret color is unique and is not represented in any commercial cultivar known to the inventor.

In the following description color references are made to The Royal Horticultural Society Colour Chart. The exact color of the red part of the ray floret color is not represented in the R.H.S. Colour Chart and the values given are believed to be closest to the actual ray floret color of Pelee. The color values were determined on plant material grown as a pinched disbudded pot mum in Salinas, Calif., on Mar. 26, 1991.

Classification:

*Botanical.*—*Dendranthema grandiflora* cv Pelee.

*Commercial.*—Daisy disbud mum.

INFLORESCENCE

A. Capitulum:

*Form.*—Flat.

*Type.*—Daisy.

*Diameter across face.*—114 to 124 mm when fully opened.

B. Corolla of ray florets:

*Color (general tonality from a distance of three meters).*—Bi-colored red and yellow.

*Color (upper surface).*—Base color is 14A, overlaid with red closest to 42A.

*Color (under surface).*—167B, streaked with 163B.

*Shape of petals.*—Straight, pointed, slightly ribbed.

C. Corolla of disc florets:

*Color (mature).*—14A.

*Color (immature).*—144B.

D. Reproductive organs:

*Androecium.*—Present on disc florets only; scant pollen.

*Gynoecium.*—Present on both ray and disc florets.

PLANT

A. General appearance:

*Height.*—23 to 28 cm when grown as a pinched pot mum in a 15 cm pot with 15 to 16 long days after sticking unrooted cuttings and 0 to 2 applications of 2500 ppm B-9 SP.

*Branching pattern.*—Semi-spreading, with 3 to 4 laterals after pinch.

B. Foliage:

*Color (upper surface).*—147A.

*Color (under surface).*—147B.

*Shape.*—See photograph.

I claim:

1. A new and distinct Chrysanthemum plant named Pelee, as described and illustrated.

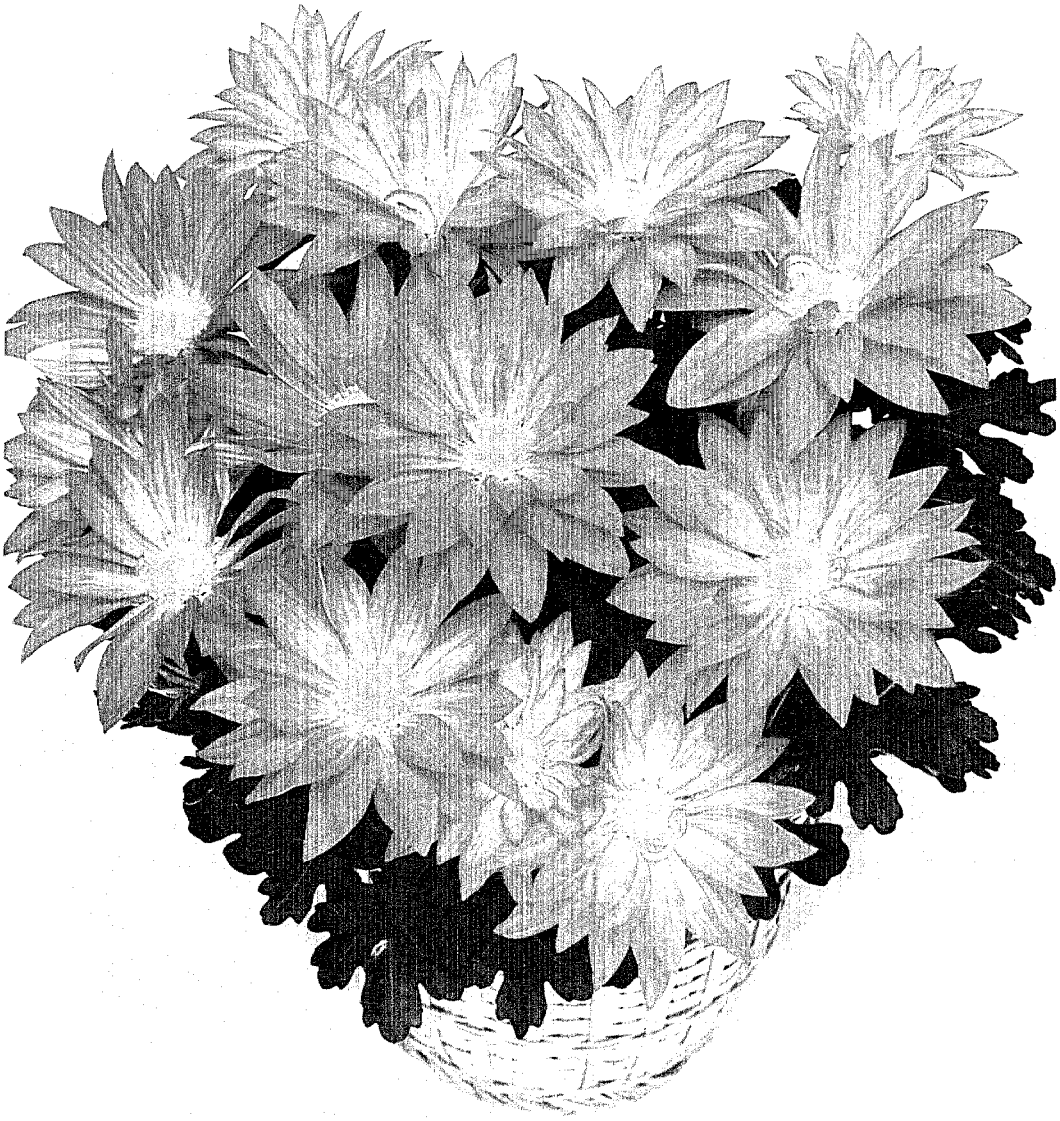

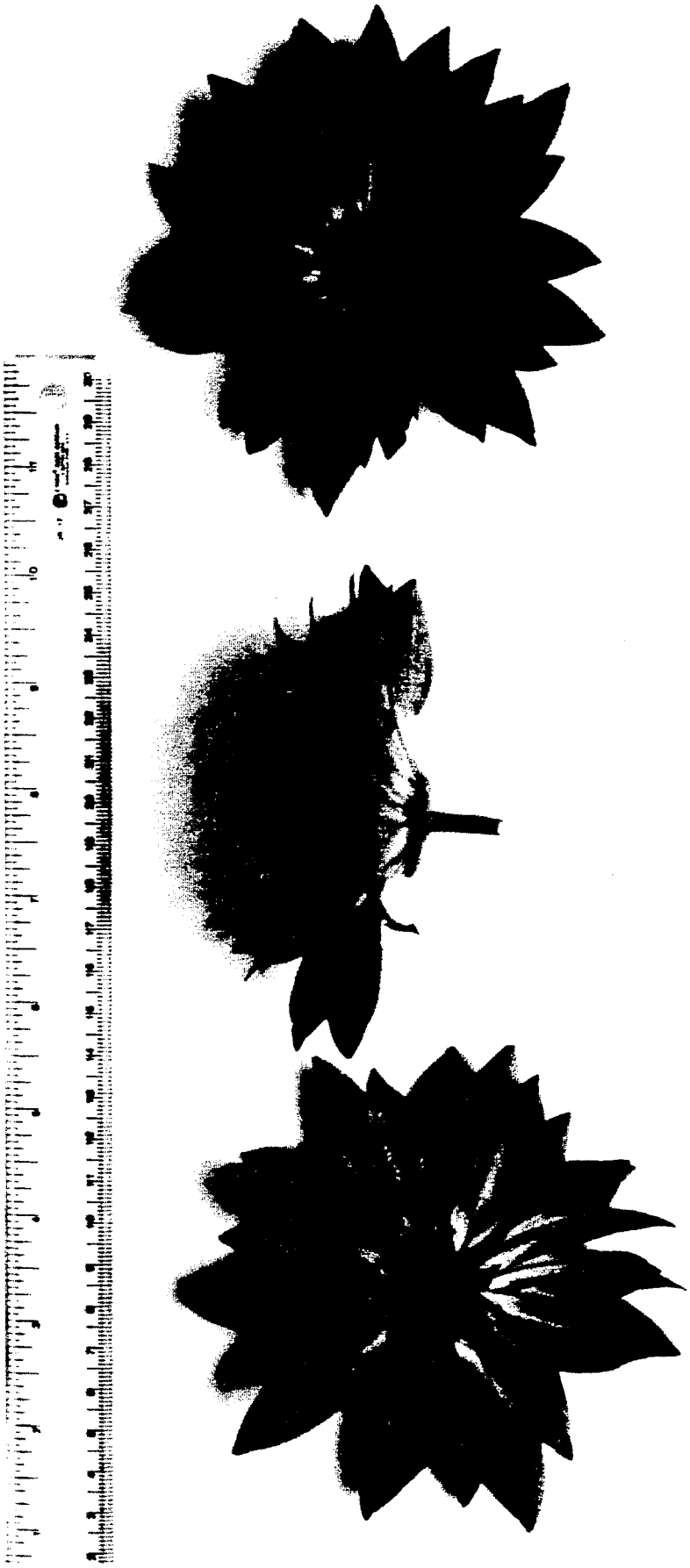

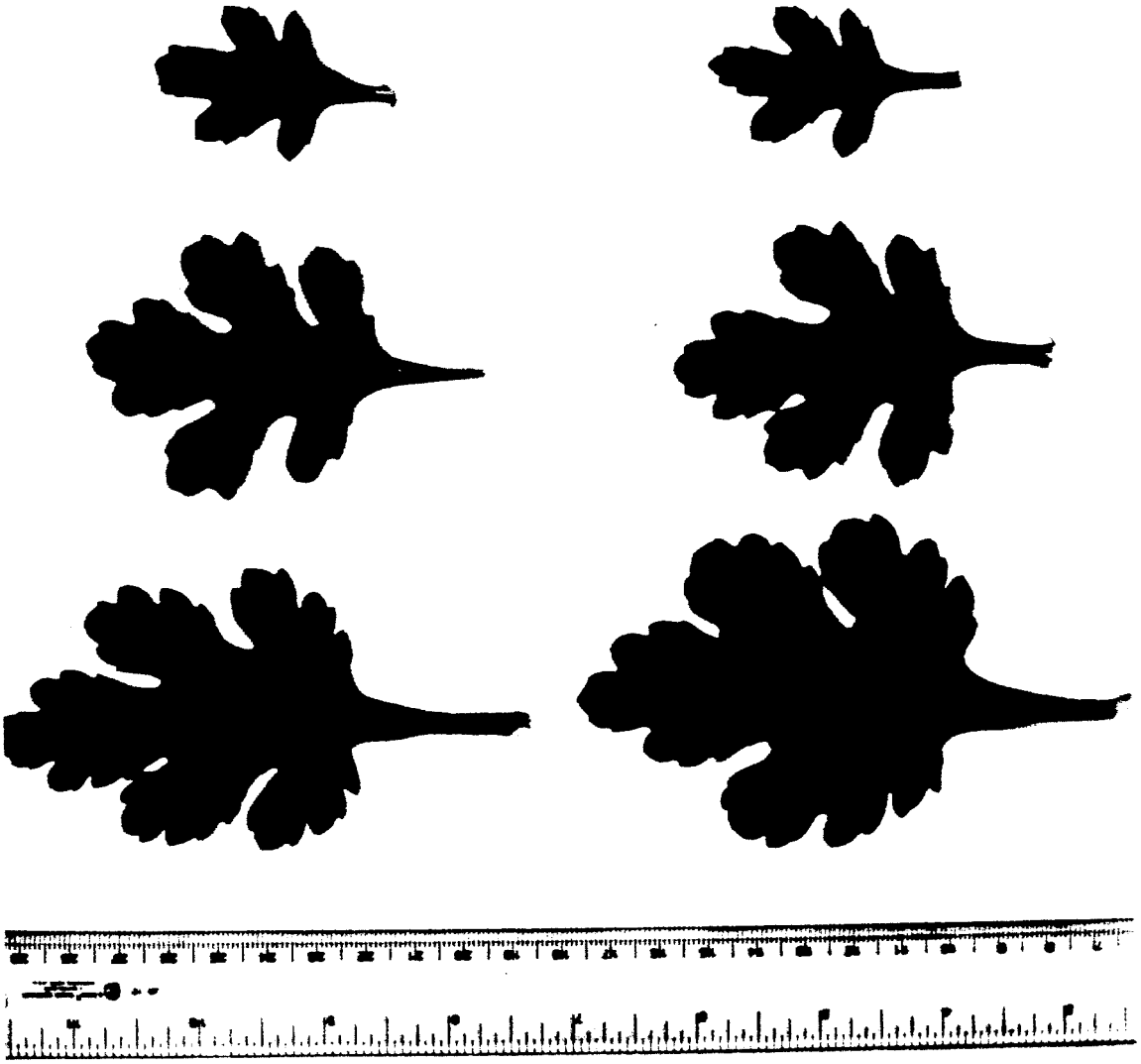

* * * * *